United States Patent [19]

Rausch et al.

[11] Patent Number: 5,840,852

[45] Date of Patent: Nov. 24, 1998

[54] METHOD FOR PRODUCING ULTRAPURE STABLE POLMERIZED HEMOGLOBIN BLOOD-SUBSTITUTE

[75] Inventors: Carl W. Rausch, Medford; Maria S. Gawryl, Charlestown; Robert A. Houtchens, Milford; Anthony J. Laccetti, North Andover; William R. Light, Natick, all of Mass.

[73] Assignee: Biopure Corporation, Cambridge, Mass.

[21] Appl. No.: 458,916

[22] Filed: Jun. 2, 1995

Related U.S. Application Data

[63] Continuation of Ser. No. 409,337, Mar. 23, 1995.
[51] Int. Cl.$^6$ .......................... C07K 14/805; A61K 38/42
[52] U.S. Cl. ................................. 530/385; 514/6
[58] Field of Search ................... 530/385; 514/6

[56] References Cited

U.S. PATENT DOCUMENTS

| | | | |
|---|---|---|---|
| 4,001,200 | 1/1977 | Bonsen et al. | 260/112.5 R |
| 4,001,401 | 1/1977 | Bonsen et al. | 424/177 |
| 4,053,590 | 10/1977 | Bonsen et al. | 424/177 |
| 4,061,736 | 12/1977 | Morris et al. | 424/177 |
| 4,826,811 | 5/1989 | Sehgal et al. | 514/6 |
| 4,857,636 | 8/1989 | Hsia | 530/385 |
| 4,861,867 | 8/1989 | Estep | 530/385 |
| 5,084,558 | 1/1992 | Rausch et al. | 530/385 |
| 5,189,146 | 2/1993 | Hsia | 530/385 |
| 5,194,590 | 3/1993 | Sehgal et al. | 530/385 |
| 5,234,903 | 8/1993 | Nho et al. | 514/6 |
| 5,296,465 | 3/1994 | Rausch et al. | 514/6 |

Primary Examiner—Cecilia J. Tsang
Assistant Examiner—Anish Gupta
Attorney, Agent, or Firm—Hamilton, Brook, Smith & Reynolds, P.C.

[57] ABSTRACT

The present invention relates to a method of therapeutically, or prophylactically, treating a vertebrate to increase tissue oxygenation, or maintain issue oxygenation, in tissue of a vertebrate wherein the tissue has a reduced red blood cell flow, and wherein the vertebrate has a normovolemic blood volume and at least a normal systemic vascular resistance. The method comprises introducing into the circulatory system of the vertebrate at least one dose of hemoglobin.

1 Claim, 3 Drawing Sheets

METHOD FOR PRODUCING ULTRAPURE STABLE POLMERIZED HEMOGLOBIN BLOOD-SUBSTITUTE

RELATED APPLICATIONS

This application is a continuing application claiming priority to U.S. Ser. No. 08/409,337, filed Mar. 23, 1995, the contents of which is incorporated herein by reference in its entirety.

BACKGROUND OF THE INVENTION

Classically, the transfer of oxygen to tissue locations in humans and other vertebrate animals has been defined as being functionally dependent upon red blood cell (RBC) flux associated with the tissue, specifically the flow rate and hematocrit of RBCs, and upon the difference in oxygen content between arterial and venous RBCs. Further, the amount of oxygen transfer from the flow of other components of the circulatory system, such as plasma, typically has been a negligible fraction of the total oxygen delivered by the RBCs. Normally, RBCs contain about 98% of the arterial oxygen content. Thus, a condition leading to a localized, regionalized and/or systemic reduction in the circulation of RBCs, often resulting from a blood vessel constriction or occlusion, or from a reduced number of normal RBCs in the cardiovascular system, can result in local, regional or systemic tissue hypoxia, tissue death and possibly even in the death of the human or other vertebrate.

Current methods for treating many causes of tissue hypoxia, particularly hypoxia resulting from a reduction in RBC flow, are typically ineffectual and/or require long, time-consuming procedures before restoring adequate oxygen delivery to the hypoxic tissue.

Therefore, a need exists for a faster more effective method of delivering oxygen to hypoxia tissue having inadequate RBC flow.

SUMMARY OF THE INVENTION

The present invention relates to a method for increasing tissue oxygenation in tissue of a vertebrate, while the tissue has reduced red blood cell flow, and wherein the vertebrate has a normovolemic blood volume and at least a normal systemic vascular resistance, comprising introducing hemoglobin into the circulatory system of vertebrate, at least one dose of hemoglobin.

This invention has many advantages including reducing the probability and extent of tissue and/or organ hypoxia, and of possible tissue necrosis, resulting from at least a partial reduction in RBC flow. Another advantage is improved survivability for a vertebrate suffering from a significant reduction in RBC flow to a vital organ or portion thereof. This invention also allows the performance of invasive procedures, which require restriction of RBC flow, without significantly reducing oxygenation of distal tissue.

DETAILED DESCRIPTION OF THE INVENTION

Figure 1:
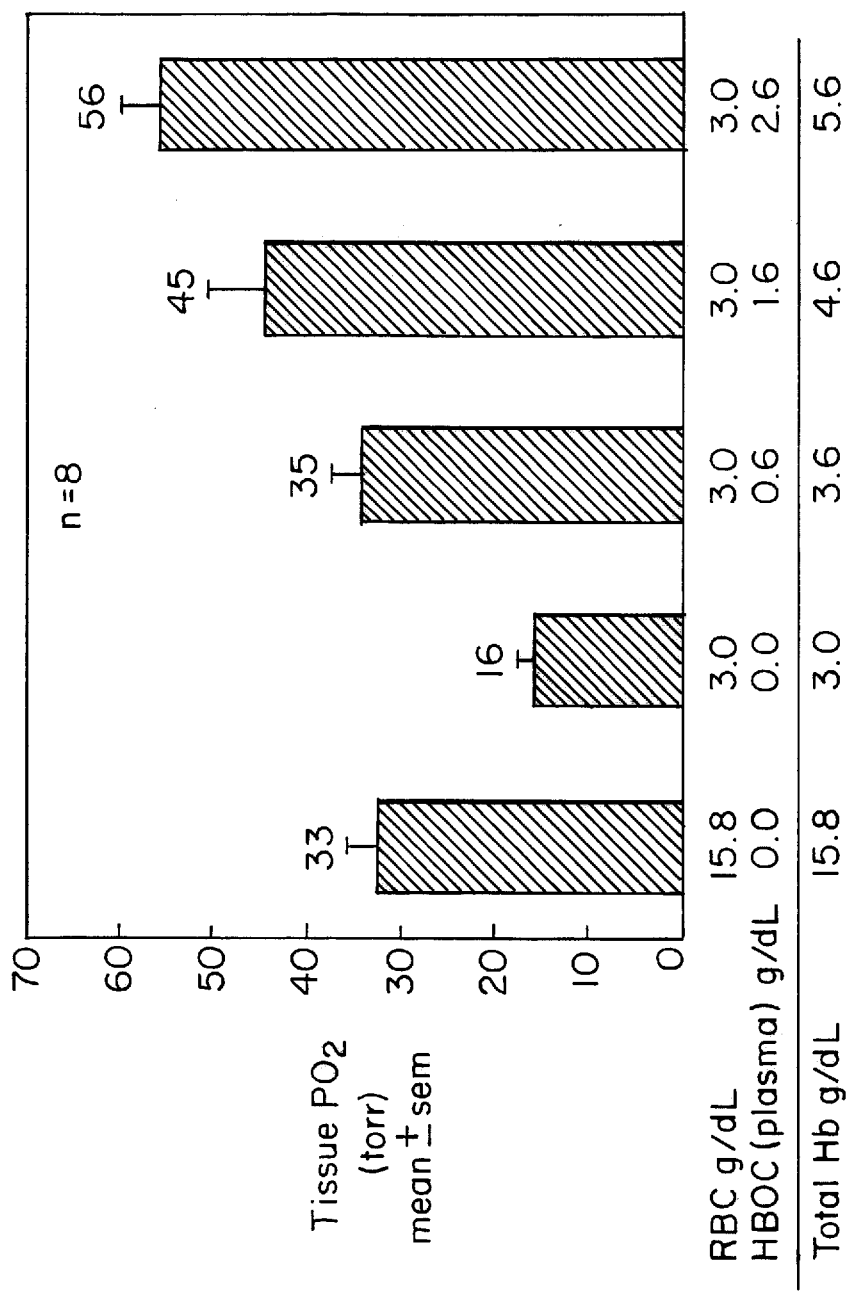
FIG. 1 is a plot of mean hind limb tissue oxygen tensions (in torr), for the experimental dogs described in Example 1, under the following conditions 1) baseline with a mean RBC hemoglobin (Hb) concentration of 15.8 g/dL, 2) after isovolemic hemodilution with hetastarch to a mean RBC hemoglobin concentration of 3.0 g/dL, 3) after isovolemic hemodilution with hetastarch, to a mean RBC hemoglobin concentration of 3.0 g/dL, and infusion of polymerized hemoglobin solution to achieve a plasma Hb concentration increase of about 0.6 g/dL, resulting in a total hemoglobin concentration of about 3.6 g/dL, 4) after isovolemic hemodilution with hetastarch, to a mean RBC hemoglobin concentration of 3.0 g/dL, and infusion of polymerized hemoglobin solution to achieve a plasma Hb concentration increase of about 1.6 g/dL, resulting in a total hemoglobin concentration of 4.6 g/dL, and 5) after isovolemic hemodilution with hetastarch, to a mean RBC hemoglobin concentration of 3.0 g/dL, and infusion of polymerized hemoglobin solution to achieve a plasma Hb concentration increase of about 2.6 g/dL, resulting in a total hemoglobin concentration of 5.6 g/dL.

This invention uses doses of hemoglobin, introduced into the circulatory system, to increase tissue oxygenation of tissue affected by a reduction in red blood cell (RBC) flow to the tissue. A reduction in RBC flow can result from a partial obstruction of RBC flow, from a reduction in the population of blood vessels associated with a tissue region, and/or from a cardiogenic dysfunction.

Oxygen transfer through a capillary to its associated tissue is typically characterized in terms of oxygen flux, which is defined as the mass of oxygen transported through the capillary per unit time. Classically, oxygen flux has been primarily associated with red blood cell flux, as RBCs normally carry 98% of the oxygen in arterial blood. Thus, when RBC flow through a capillary is significantly reduced, oxygen flux is reduced, thereby resulting in less oxygen transfer to the associated tissue, and possibly tissue hypoxia or tissue anoxia.

The method of this invention utilizes the capacity of hemoglobin, separate from RBCs, to carry oxygen within the plasma phase of the circulatory system and to transfer oxygen to tissue. Thus, for a vertebrate who has been administered hemoglobin by introducing the hemoglobin into the circulatory system of the vertebrate, oxygen flux also depends on the increase in oxygen transferred by the administered hemoglobin when circulated through the vertebrate's circulatory system.

The oxygen transfer capacity of hemoglobin, circulated in the circulatory system, is demonstrated in Example 1, wherein anemic hypoxia within muscle tissue, as defined by a measured reduction in the tissue oxygen tension, which was induced by isovolemic hemodilution with hetastarch, was effectively treated by intravascularly administering small doses of a hemoglobin solution to the test subjects.

In the method of invention, tissue oxygenation at least partially occurs as a result of the transfer of oxygen from hemoglobin, circulated in the plasma phase of the circulatory system, to a tissue of a vertebrate. The tissue being oxygenated can be a small localized tissue area; a regionalized tissue area, such as a limb or organ; and/or tissue throughout the body of the vertebrate. Tissue with a reduced oxygen supply, resulting from reduced RBC flow to the affected tissue, can become hypoxic, as measured by a reduction in tissue oxygen tension, and even anoxic under extreme conditions, such as a prolonged complete restriction in oxygen supply.

Tissue hypoxia is a decrease in the oxygen tension (partial pressure of oxygen) below normal levels within the tissue. Tissue anoxia is a condition with no measurable oxygen partial pressure within the tissue.

Tissue oxygenation, which is measured in terms of oxygen tension (oxygen partial pressure) within the tissue, is determined as described in Example 1.

Additionally in this method, the definition of circulatory system is as classically defined, consisting of the heart, arteries, veins and microcirculation including smaller vascular structures such as capillaries.

Further, a vertebrate is as classically defined, including humans, or any other vertebrate animals which uses blood in a circulatory system to transfer oxygen to tissue. A preferred vertebrate for the method of invention is a mammal, such as a human, an other primate, a dog, a cat, a rat, a horse or a sheep. A vertebrate treated in the method of invention can be a fetus (prenatal vertebrate), a post-natal vertebrate, or a vertebrate at time of birth.

A vertebrate, having a localized, regional or systemic reduction in RBC flow, can have oxygen transport systems which are otherwise normal, or can have additional abnormalities which can deleteriously affect oxygen transport and transfer in a portion of the body, or throughout the body as a whole.

In addition, in this method the vertebrate has a normovolemic blood volume prior to administration of the hemoglobin. A normovolemic blood volume is defined as a volume of blood within the circulatory system of the vertebrate which will not result in hypovolemic shock, such as can result from a major hemorrhage or a large loss of fluid secondary to vomiting, diarrhea, burns or dehydration. Typically, a normovolemic blood volume includes at least about 90% of the normal volume of blood for that vertebrate. In some cases a normovolemic volume can contain as little as about 80% of the normal blood volume without resulting in hypovolemic shock.

Furthermore, the blood constituting the normovolemic blood volume, contains at least about a normal concentration of RBCs. For example, the blood in a normovolemic blood volume of a human typically has a major vessel hematocrit of at least about 30%.

In this method, a vertebrate also has a normal, or higher than normal, systemic vascular resistance in the circulatory system, prior to administering the hemoglobin. A normal systemic vascular resistance is a vascular resistance which would not result in distributive shock, such as septic shock, in the vertebrate.

Reduced red blood cell flow includes any reduction in RBC flow, either localized, regionalized and/or systemic, below normal RBC flow levels, including a "no RBC flow" condition. Localized RBC flow consists of RBC flow through one or more capillaries within a capillary bed, wherein said capillaries would normally provide RBC flow to oxygenate a localized tissue area. Regionalized RBC flow provides RBC flow to oxygenate a larger tissue area, such as a limb or organ. Systemic RBC flow is flow through the major circulatory systems of the body, thus providing RBCs to oxygenate the body as a whole.

In one embodiment of the method of invention, hemoglobin is administered to a vertebrate who has, or will have, a partial obstruction of the circulatory system, such as a stenosis or vascular blockage, in an amount that reduces or precludes RBC flow past the partial obstruction, but by which at least some plasma can flow. Administering hemoglobin increases tissue oxygenation in tissue distal to a localized or regionalized partial obstruction, and/or to increases tissue oxygenation throughout the body to treat a systemic partial obstruction.

In this method, the partial obstruction has at least one opening through which a plasma component, such as molecular hemoglobin, can flow to the affected tissue, wherein the plasma component has a molecular weight of about 16,000 Daltons or more. Preferably, the partial obstruction has at least one opening through which plasma components, with a molecular weight of about 32,000 Daltons or more (e.g., dimeric Hb) can flow to the affected tissue. More preferably, plasma components, having a molecular weight of about 64,000 Daltons or more, such as intramolecularly cross-linked tetrameric Hb, can flow past the partial obstruction to the affected tissue.

RBCs are significantly larger than hemoglobin, typically being 7–10 microns in diameter, therefore requiring significantly larger vascular openings, than does hemoglobin, to flow past a partial obstruction.

Partial obstructions can occur at all tissue locations and in all blood vessels, such as arteries, veins and capillaries. In addition, valves within the circulatory system, such as aortic, mitral and tricuspid valves, can also be partially obstructed. Further, chamber or sections of the heart can be partially obstructed, such as ventricular outflows and the ventricular opening to the pulmonary artery.

A partial obstruction of the circulatory system can be temporary, permanent or recurrent. A circulatory system partial obstruction can be caused by various means, such as vessel wall defects, disease, injury, aggregation of blood components, neoplasms, space-occupying lesions, infections, foreign bodies, compression, drugs, mechanical devices, vasoconstriction and vasospasms.

A stenosis of the circulatory system, as defined herein, is a narrowing of any canal, or lumen, in the circulatory system. Typically, a stenosis can result from disease, such as atherosclerosis; a vessel wall abnormality, such as a suture line from an arterial graft, a junction point of attachment for a graft or stent, a kink or deformity in a vessel, graft or stent, healed or scarred tissue from an injury or invasive procedure (e.g., catheterization, angioplasty, vascular stenting, vascular grafting with prosthesis, allogenic tissue and/or autologous tissue); a vascular prosthesis such as an artificial valve or vessel; compression, such as by a neoplastic mass, hematoma or mechanical means (e.g., clamp, tourniquet or cuff device); chemical poisoning or drug side effects; vasoconstriction; and vasospasms.

Examples of stenosis within valves or sections of the heart include aortic stenosis, buttonhole stenosis, calcific nodular stenosis, coronary ostial stenosis, double aortic stenosis, fish-mouth mitral stenosis, idiopathic hypertrophic subaortic stenosis, infundibular stenosis, mitral stenosis, muscular subaortic stenosis, pulmonary stenosis, subaortic stenosis, subvalvar stenosis, supravalvar stenosis, tricuspid stenosis.

Vascular blockage is defined herein as a blockage within a canal or lumen of the circulatory system. Typical examples of blockages within a canal or lumen include in situ or embolized atheromatous material or plaques, aggregations of blood components, such as platelets, fibrin and/or other cellular components, in clots resulting from disease or injury or at the site of wound healing. Clots include thrombosis, embolisms and in an extreme case, abnormal coagulation states.

Other vascular blockages include blockages resulting from an infection by a microorganism or macroorganism within the circulatory system, such as fungal or heartworm infections.

Further, vascular blockages can result from foreign bodies contained within any canal or lumen in the circulatory system, such as a "GELFOAM®" absorbable gelatin sterile sponge for blocking blood flow during an invasive medical procedure, or a broken catheter tip.

In another embodiment of the method of invention, hemoglobin is administered to a vertebrate who has, or will have, a reduction in the population of functioning blood vessels supplying RBCs to a tissue area, with a consequential reduction in RBC flow to the affected tissue, whereby the administered hemoglobin increases tissue oxygenation for the affected tissue. A reduction in the population of blood vessels typically is the result of a burn (thermal, chemical or radiation) or of an invasive medical procedure, such as removing or cauterizing blood vessels.

In yet another embodiment of the method of invention, hemoglobin is administered to a vertebrate who has reduced systemic blood flow, and thus reduced RBC flow, due to a cardiogenic dysfunction, whereby the administered hemoglobin increases tissue oxygenation for tissue throughout the body. Cardiogenic dysfunctions are diseases, or injuries, of the heart, or affecting the heart, which result in low blood flow conditions, such as myocardial infarction, myocardial ischemia, myocardial injury, arrhythmia, cardiomyopathy, cardioneuropathy and pericardial effusion.

In this method, a partial obstruction of the circulatory system of a prenatal vertebrate is typically the result of a disease or defect affecting prenatal development during gestation, or from treatment of a disease or defect (e.g., in-utero surgery).

The improvement in oxygen transfer to tissue affected by reduced RBC flow, by intravascular administration of a hemoglobin solution, is demonstrated by the significant increases in tissue oxygenation, observed in Examples 1 and 2, following the intravascular infusion of sufficient doses of a hemoglobin solution to restore tissue oxygen tensions to baseline values.

The hemoglobin, when used in the method of invention, is not contained in a natural RBC, but rather, is typically present in a physiologically acceptable carrier. It is preferred that the carrier be in a liquid state. It is also preferred that the hemoglobin is present within a physiologically acceptable solution or suspension of hemoglobin within a physiologically acceptable carrier. Suitable hemoglobins include any form of hemoglobin, such as dimeric hemoglobin, tetrameric hemoglobin, intramolecularly cross-linked hemoglobin, polymerized hemoglobin, freeze-dried hemoglobin, and/or chemically modified hemoglobin, wherein a significant portion of the hemoglobin is capable of transporting and transferring oxygen. Hemoglobin has a significant capability to transport and transfer oxygen if administration of the hemoglobin, into the circulatory system of a vertebrate, results in a measurable increase in tissue oxygen tension for hypoxic tissue in the body of the vertebrate. Preferably, at least about 85% of the hemoglobin is capable of transporting and transferring oxygen.

Hemoglobin suitable for the method of invention can be derived from new, old or outdated blood from humans and/or other mammals, such as cattle, pigs and sheep. In addition, transgenically-produced hemoglobin, such as the transgenically-produced hemoglobin described in *BIO/TECHNOLOGY*, 12: 55–59 (1994), and recombinantly produced hemoglobin, such as the recombinantly produced hemoglobin described in *Nature*, 356: 258–260 (1992), are also suitable for a hemoglobin solution of the method of invention.

Examples of suitable hemoglobin solutions include hemoglobin solutions which have a stabilized 2,3-diphosphoglycerate level, as described in U.S. Pat. No. 3,864,478, issued to Bonhard; cross-linked hemoglobin, as described in U.S. Pat. No. 3,925,344, issued to Mazur, or in U.S. Pat. Nos. 4,001,200, 4,001,401 and 4,053,590, issued to Bonsen et al., or in U.S. Pat. No. 4,061,736, issued to Morris et al., or in U.S. Pat. No. 4,473,496, issued to Scannon; stroma-free hemoglobin, as described in U.S. Pat. No. 3,991,181, issued to Doczi, or in U.S. Pat. No. 4,401,652, issued to Simmonds et al. or in U.S. Pat. No. 4,526,715, issued to Kothe et al.; hemoglobin coupled with a polysaccharide, as described in U.S. Pat. No. 4,064,118, issued to Wong; hemoglobin condensed with pyridoxal phosphate, as described in U.S. Pat. No. 4,136,093, issued to Bonhard et al.; dialdehyde-coupled hemoglobin, as described in U.S. Pat. No. 4,336,248, issued to Bonhard et al.; hemoglobin covalently bound with inulin, as described in U.S. Pat. No. 4,377,512, issued to Ajisaka et al.; hemoglobin or a hemoglobin derivative which is coupled with a polyalkylene glycol or a polyalkylene oxide, as described in U.S. Pat. No. 4,412,989, issued to Iwashita et al., or U.S. Pat. No. 4,670,417, issued to Iwasaki et al., or U.S. Pat. No. 5,234,903, issued to Nho et al.; pyrogen- and stroma-free hemoglobin solution, as described in U.S. Pat. No. 4,439,357, issued to Bonhard et al.; stroma-free, non-heme protein-free hemoglobin, as described in U.S. Pat. No. 4,473,494, issued to Tye; modified cross-linked stroma-free hemoglobin, as described in U.S. Pat. No. 4,529,719, issued to Tye; stroma-free, cross-linked hemoglobin, as described in U.S. Pat. No. 4,584,130, issued to Bucci et al.; α-cross-linked hemoglobin, as described in U.S. Pat. Nos. 4,598,064 and Re. 34,271, issued to Walder et al.; tetramer-free polymerized, pyridoxylated hemoglobin, as described in U.S. Pat. Nos. 4,826,811 and 5,194,590, issued to Sehgal et al.; stable aldehyde polymerized hemoglobin, as described in U.S. Pat. No. 4,857,636, issued to Hsia; hemoglobin covalently linked to sulfated glycosaminoglycans, as described in U.S. Pat. No. 4,920,194, issued to Feller et al.; modified hemoglobin reacted with a high molecular weight polymer having reactive aldehyde constituents, as described in U.S. Pat. No. 4,900,780, issued to Cerny; hemoglobin cross-linked in the presence of sodium tripolyphosphate, as described in U.S. Pat. No. 5,128,452, issued to Hai et al.; stable, polyaldehyde polymerized hemoglobin, as described in U.S. Pat. No. 5,189,146, issued to Hsia; and β-cross-linked hemoglobin, as described in U.S. Pat. No. 5,250,665, issued to Kluger et al.

Hemoglobin suspensions include hemoglobin in emulsions or emulsified hemoglobin solutions. Examples of hemoglobin suspensions include hemoglobin solutions which have a hemoglobin fraction encapsulated within water immiscible amphiphylic membranes, as described in U.S. Pat. No. 4,543,130, issued to Djordjevich et al.; an emulsion of two aqueous phases to which stroma-free hemoglobin is added, as described in U.S. Pat. No. 4,874,742, issued to Ecanow et al.; and a water-in-oil-in-water multiple emulsion of hemoglobin solution in a physiologically compatible oil, as described in U.S. Pat. Nos. 5,061,688 and 5,217,648, issued to Beissinger et al.

In a preferred embodiment, hemoglobin used in the method of invention is in the form of a polymerized hemoglobin blood-substitute. A blood-substitute, as defined herein, is a hemoglobin-based oxygen carrying composition which is capable of transporting and transferring oxygen to at least vital organs and tissues. Examples of suitable polymerized hemoglobin blood-substitutes are described in U.S. Pat. Nos. 5,084,558 and 5,217,648, issued to Rausch et al. and also in Examples 4 and 5.

The teachings of the patents noted above are incorporated herein by reference.

The composition of hemoglobin solutions, or blood-substitutes, preferred for use in the method of invention are sterile solutions having less than 0.5 endotoxin units/mL, a methemoglobin content that will not result in a significant reduction in oxygen transport/transfer capacity, a total hemoglobin concentration between about 2 to about 20 g Hb/dL, a physiologic pH and a chloride ion concentration of less than 35 meq/L. In an even more preferred embodiment, the Hb solution has a total hemoglobin concentration between about 12 to about 14 g Hb/dL. Examples of preferred Hb solutions and blood-substitutes are described in U.S. Pat. No. 5,296,465, issued to Rausch et al. and in Example 4.

Typically, a suitable dose, or combination of doses, of hemoglobin is an amount of hemoglobin which, when contained within the blood plasma, will result in an increase in total hemoglobin concentration in a vertebrate's blood between about 0.1 to about 10 grams Hb/dL. A preferred dose for humans will increase total hemoglobin between about 0.5 to about 2 g Hb/dL. A preferred dose for dogs will increase total hemoglobin between about 3.5 to about 4.5 g Hb/kg body weight.

Hemoglobin can be administered into the circulatory system by injecting the hemoglobin directly and/or indirectly into the circulatory system of the vertebrate, by one or more injection methods. Examples of a direct injections methods include intravascular injections, such as intravenous and intra-arterial injections, and intracardiac injections. Examples of indirect injections methods include intraperitoneal injections, subcutaneous injections, such that the hemoglobin will be transported by the lymph system into the circulatory system, injections into the bone marrow by means of a trocar or catheter. Preferably, the hemoglobin is administered intravenously.

The vertebrate being treated can be normovolemic or hypervolemic prior to, during, and/or after infusion of the Hb solution. The hemoglobin can be directed into the circulatory system by methods such as top loading and by exchange methods.

Hemoglobin can be administered therapeutically, to treat hypoxic tissue within a vertebrate resulting from a reduced RBC flow in a portion of, or throughout, the circulatory system. Further, hemoglobin can be administered prophylactically to prevent oxygen-depletion of tissue within a vertebrate, which could result from a possible or expected reduction in RBC flow to a tissue or throughout the circulatory system of the vertebrate. Further discussion of the administration of hemoglobin to treat a partial arterial obstruction, therapeutically or prophylactically, or a partial blockage in microcirculation, is provided in Examples 2 and 3, respectively.

The invention will be further illustrated by the following examples.

EXAMPLE 1

Study of Tissue Oxygenation from Infusing Polymerized Hemoglobin Solution after Hemodilution In this study, regional tissue oxygenation levels were measured in the left hind limb muscle (m. gastrocnemius), within an 8-dog experimental group, to determine the effects of infusion of polymerized hemoglobin solution upon animals made anemic by isovolemic hemodilution with a non-oxygen bearing solution.

Regional tissue oxygen partial tensions were determined, using a Sigma-$pO_2$-Histograph (Model No. KIMOC 6650, Eppendorf-Netherler-Hinz GmbH, Hamburg, Germany), to measure at least 200 local $pO_2$ values in the skeletal musculature distal to the exposed femoral artery, and then display the $pO_2$ values in a histogram for each measurement point.

At each measurement point, the Eppendorf $pO_2$-Histograph measured oxygen partial pressure polarographically with an oxygen needle probe having a spring steel casing containing a glass-insulated, teflon-coated gold microcathode. The oxygen needle probe was polarized with −700 mV towards an Ag/AgCl anode, which was attached to the skin near the site of the oxygen needle probe insertion. The resulting current was proportional to the oxygen partial pressure at the electrode tip, thus giving a measurement of local tissue oxygenation.

Regional oxygenation measurements were obtained automatically with the aid of a microprocessor-controlled manipulator, which moved the oxygen needle probe through the tissue in a series of "pilgrim steps", each typically consisting of a forward motion of 1 mm followed by a backward motion of 0.3 mm, to relieve compression of the tissue from the forward motion, with subsequent $pO_2$ value sampling. At the end of each tissue oxygenation measurement, the needle probe was moved to a new tissue location, such that each measurement was performed only in undisturbed, non-traumatized muscle tissue.

In this study, 8 dogs were given, by the intramuscular injection, 5 mg/kg ketamine (Ketanest™, Parke-Davis, Germany) and 2 mg/kg xylazine (Rompun™, Bayer, Germany) for induction of anesthesia 30 minutes prior to endotracheal intubation. Mechanical ventilation was performed with 70% nitrous oxide in oxygen and 1.0% isoflurane. Ventilation was set to maintain end-tidal $pCO_2$ between 34 and 38 mm Hg.

The left femoral artery was cannulated for invasive measuring of arterial blood pressure and blood sampling. A 7-Swan-Ganz catheter was placed in the pulmonary artery via the right femoral vein for monitoring pulmonary artery pressure, central venous pressure and pulmonary capillary wedge pressure. A 3 mm catheter was placed in the right external jugular vein and the left femoral vein for blood exchange, and for polymerized hemoglobin solution infusion.

Following surgical preparation, anesthesia was maintained by continuous infusion of 0.025 mg/kg/hr fentanyl (Janssen, Germany) and 0.4 mg/kg/hr midazolam (Dormicum™, Roche, Germany). Muscle relaxation was achieved with 0.2 mg/kg/hr vecuronium (Norcuron™, Organon, Germany). Ventilation was set at 30% oxygen in air.

The dogs were allowed to equilibrate for 40 minutes before taking baseline readings. Following baseline readings, each dog was isovolemically hemodiluted with hetastarch from a baseline hematocrit of about 35–45% to a hematocrit of about 25%, and then step-wise in about 5% increments, to final hematocrits of about 10%. At hematocrits of about 25%, 20%, 15% and 10%, associated hemodynamic and tissue oxygen partial pressures were measured.

After achieving hematocrits of about 10%, which was equivalent to a RBC hemoglobin concentration in the blood of about 3 g Hb/dL of blood, each dog was then infused with a polymerized hemoglobin solution (HBOC-201, also known as Hemopure 2™ Solution, Biopure Corporation, Boston, Mass.) in three incremental doses sufficient to raise the measured total hemoglobin (Hb from RBCs plus Hb from polymerized Hb solution) by about 0.6–1.0 g/dL per dose. Further description of or Hemopure 2™ Solution is provided in Example 5.

All parameters were recorded after an equilibration period of 20 minutes. The time periods between the respective total hemoglobin levels was 60 minutes.

FIG. 1 shows that the infusion of polymerized hemoglobin solution substantially increased regional muscle tissue oxygen tensions in anemic dogs, after the first dose of polymerized hemoglobin solution, from a mean $pO_2$ of 16 torr, associated with a RBC hemoglobin concentration of 3.0 g/dL, to a normal mean $pO_2$ of 35 torr by increasing total hemoglobin concentration by about 0.6 g/dL from the infusion of polymerized hemoglobin solution. The experimental dogs of this study had mean muscle tissue oxygen tensions of 33 torr, prior to hemodilution, which was associated with a RBC hemoglobin concentration of about 15.8 g/dL. Consequently, this study demonstrated that reduced muscle tissue oxygen tensions, which resulted from decreased availability of RBCs to transfer oxygen to the tissue, can be improved and even restored to normal values, or above normal values, by infusing small amounts of hemoglobin into the circulatory systems of the animals. For instance, FIG. 1 demonstrates that an increase in total hemoglobin of about 0.6 g Hb/dL plasma, from an infusion of polymerized hemoglobin solution, raised tissue oxygen tension by 19 torr, which was equivalent to the reduction in tissue oxygen tension associated with an decrease in RBC hemoglobin concentration of about 12.8 g Hb/dL plasma from hemodilution.

EXAMPLE 2

Study of Tissue Oxygenation Distal to an Arterial RBC Flow Blockage

In this study, tissue oxygen tensions were measured in the hind limb muscle (m. gastrocnemius) at points distal to a 90–93% femoral artery stenosis in a Control Group (6-dogs) and a 94% femoral artery stenosis in Experimental Group A (7-dogs), following post-stenotic infusion of increasing levels of polymerized hemoglobin solution (Hemopure 2™ Solution, Biopure Corporation, Boston, Mass.). This study also included measurement of tissue oxygen tensions in the hind limb muscle at points distal to a 94% femoral artery stenosis in Experimental Group B (6-dogs), in which polymerized hemoglobin solution (HBOC-201) was infused prior to inducing the stenosis.

All parameters were recorded at baseline, after an equilibration period of 30 minutes following stenosis, 45 minutes after stenosis (Experimental Group B only) and 15 minutes after dosing with polymerized hemoglobin solution or hetastarch (2-hydroxyethyl ether) (Control Group and Experimental Group A only).

The dogs in the Control and Experimental Groups were anesthetized and monitored as described in Example 1. Following induction of anesthesia, baseline measurements were recorded. Baseline regional tissue oxygen tensions for the hind limb muscle of the Control Group and Experimental Group A are provided in FIG. 2.

Figure 3:
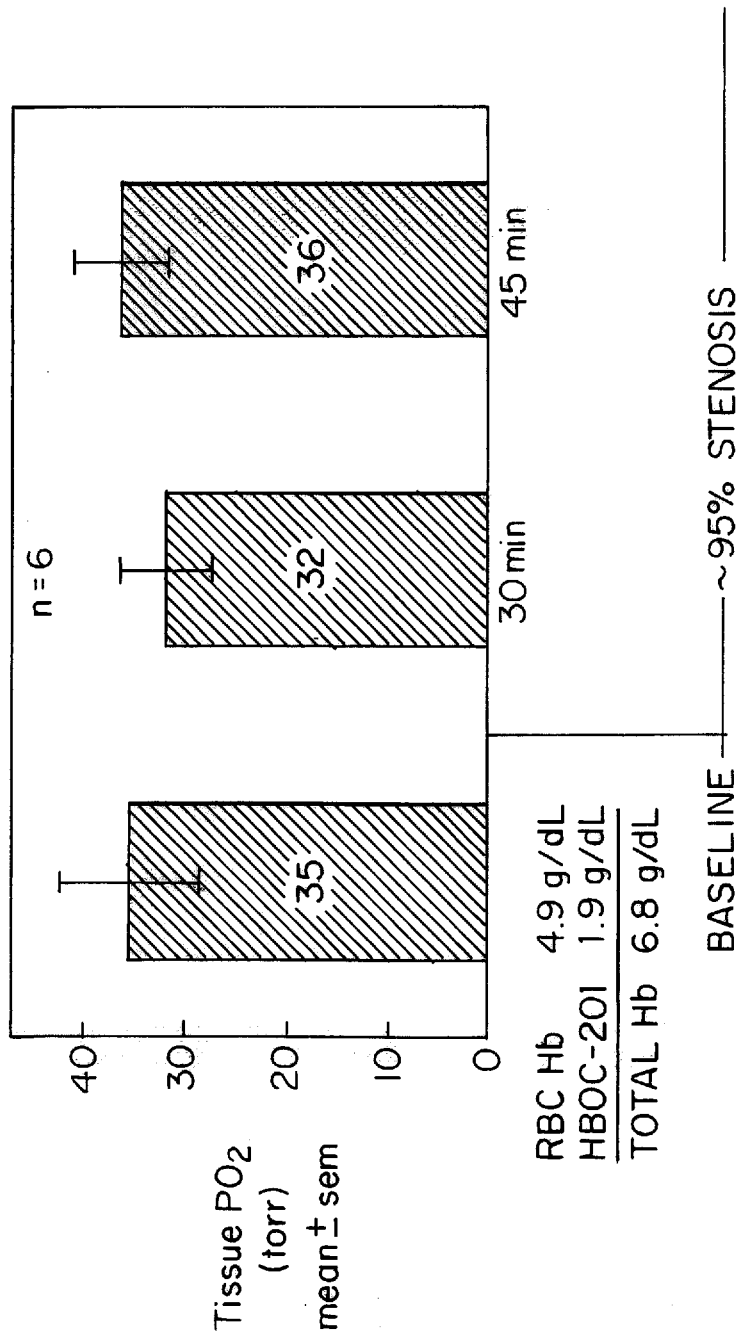
FIG. 3 is a plot of mean hind limb tissue oxygen tensions (in torr) for the Experimental Group B dogs, described in Example 2, in which a 94% femoral artery stenosis was induced in a hind limb of each dogs after intravenously injecting amounts of polymerized hemoglobin solution into in the general circulatory system of each of the dogs proximal to the future stenosis, in an amount sufficient to increase total hemoglobin concentration by about 2 grams per deciliter. The plot provides mean hind limb tissue oxygen tensions for the following conditions 1) baseline, 2) 30 minutes after establishing a 94% femoral artery stenosis in each dog, and 3) 45 minutes after establishing a 94% femoral artery stenosis in each dog.

Each of the dogs of Experimental Group B were then intravenously infused with an amount of polymerized hemoglobin solution sufficient to increase the measured total hemoglobin in each dog (Hb from RBCs plus Hb from polymerized Hb solution in the plasma) by about 2.0 g/dL. The conditions of the Group B dogs were subsequently allowed to equilibrate for about 15 to about 30 minutes and tissue oxygen tensions were recorded as baseline values for Experimental Group B (FIG. 3).

Figure 2:
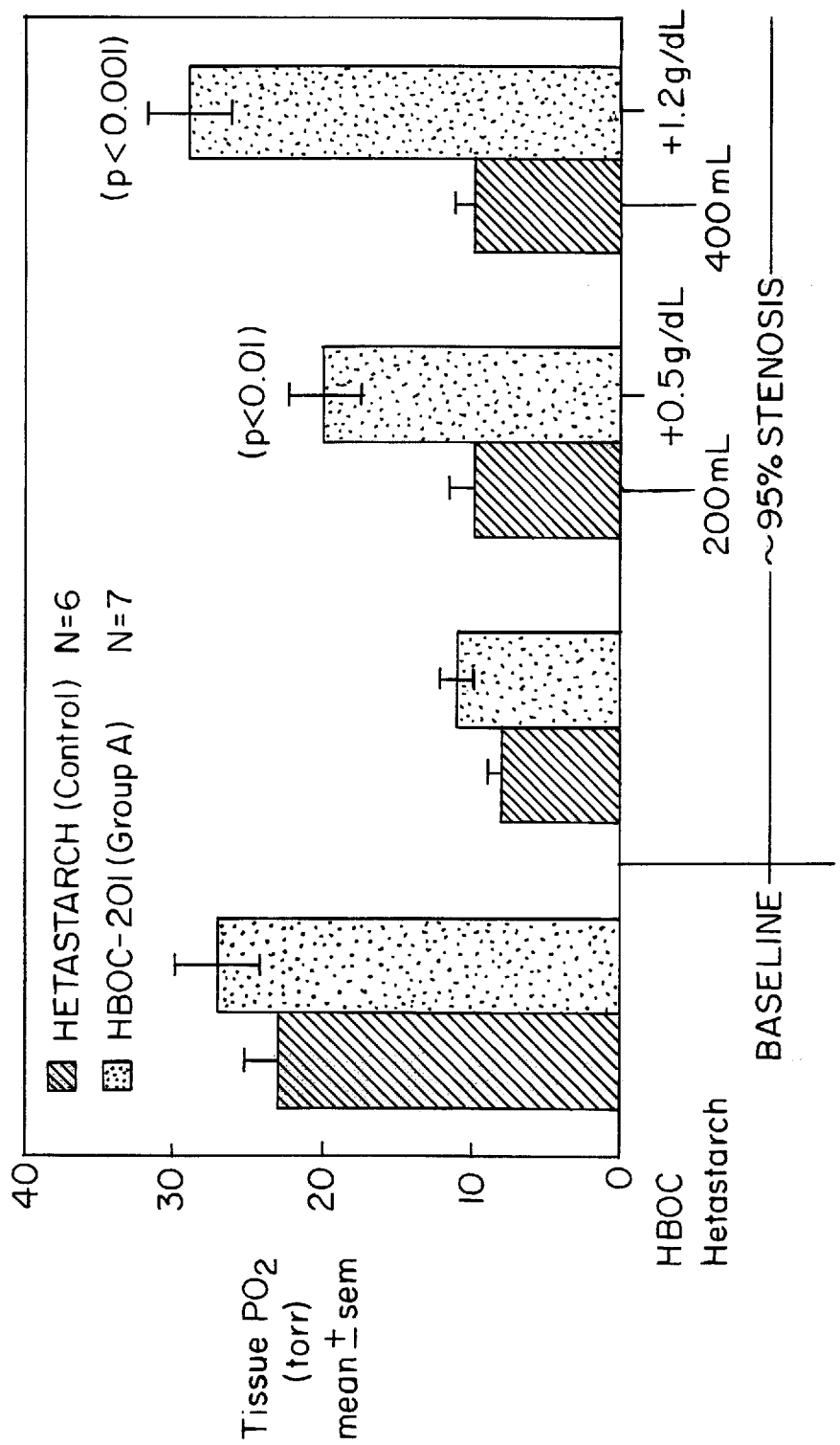
FIG. 2 is a plot of mean hind limb tissue oxygen tensions (in torr), for the control dogs as compared to the Experimental Group A dogs, described in Example 2, for the following conditions 1) baseline, 2) 30 minutes after establishing a femoral artery stenosis in each dog (i.e. a 94% stenosis for the Experimental Group A dogs and a 90–93% stenosis for the Control Group dogs), 3) 30 minutes after intravenously injecting amounts of polymerized hemoglobin solution into the experimental dogs (or equivalent volumes of hetastarch solution into the control dogs), in the general circulatory system of each of the dogs proximal to the stenosis, in an amount sufficient to increase plasma hemoglobin concentration by about 0.5 grams per deciliter, and 4) 30 minutes after intravenously injecting amounts of polymerized hemoglobin solution into the experimental dogs (or equivalent volumes of hetastarch solution into the control dogs), in the general circulatory system of each of the dogs proximal to the stenosis, in an amount sufficient to increase plasma hemoglobin concentration by about 1.2 grams per deciliter.

The femoral artery, for one hind leg of each dog in each group, was then surgically exposed and clamped with a variable arterial clamp until blood flow was reduced by approximately 90–95%. Blood flow was measured by a circumferential flow probe located distal to the stenosis. Mean regional tissue oxygen tensions, for the hind limb muscles distal to the stenosis in the dogs of the Control Group and Experimental Group A, and of Experimental Group B, 30 minutes after stenosis, are provided in FIGS. 2 and 3, respectively. These figures show a severe equivalent decrease in tissue oxygen tensions ($pO_2$ levels), resulting in regional hypoxia in the distal hind limb muscle, for the dogs of the Control Group and Experimental Group A (FIG. 2). Specifically, as shown in FIG. 2, the mean tissue oxygen tension, for the Control Group, decreased from a mean baseline value of 23±2.2 torr to a mean post-stenotic value of 8±0.9 torr. Further, as shown in FIG. 2, the mean tissue oxygen tension, for Experimental Group A, decreased from a mean baseline value of 27±2.9 torr to a mean post-stenotic value of 11±1.1 torr. In addition, at this time the distal muscle tissue for dogs of the Control Group and Experimental Group A appeared pale gray in color.

However for the dogs of Experimental Group B, which were infused with polymerized hemoglobin solution prior to inducing the 95% stenosis, at 30 minutes post-stenosis no significant decrease in mean muscle tissue oxygen tension was observed. As shown in FIG. 3, the mean tissue oxygen tension for Experimental Group B decreased from a mean baseline value of 35±6.9 torr to a mean post-stenotic value of 32±4.5 torr.

Furthermore, 45 minutes after stenosis, the mean tissue oxygen tension, for Experimental Group B, of 36±4.5 torr was not significantly different from the baseline value.

The results in FIGS. 2 and 3 show that induction of a "≧90%" stenosis in an animal, created a severe hypoxic condition in tissue distal to the stenosis, except where the animal was prophylactically administered polymerized hemoglobin solution before inducing the stenosis. As shown in FIG. 3, animals, which were prophylactically administered polymerized hemoglobin solution, maintained normal tissue oxygen tensions in muscle tissue distal to the stenosis, thus demonstrating the efficacy of the prophylactic administration of hemoglobin in preventing tissue hypoxia subsequent to a partial blockage of RBC flow to tissue.

Subsequently to the 30 minute post-stenotic oxygen tension measurements, each dog in the Control Group was then infused with a hetastarch in two incremental doses of 200 mL, which generally corresponds in volume to the volume of polymerized hemoglobin solution needed to raise total Hb in a dog by about 0.5 to about 0.7 g/dL per dose. Concurrently, each dog in Experimental Group A was infused with polymerized hemoglobin solution in two incremental doses sufficient to raise the measured total hemoglobin in each dog (Hb from RBCs plus Hb from polymerized Hb solution) by about 0.5 to about 0.7 g/dL per dose.

Post-infusion regional tissue oxygen tensions for the stenotic hind limb muscles of the control group, for 200 mL and 400 mL hetastarch infusions, are provided in FIG. 2. The mean tissue oxygen tensions observed were 10±1.6 torr for the 200 mL hetastarch infusion and 10±1.2 torr for the 400 mL hetastarch infusion. This figure shows that the post-stenotic infusion of hetastarch did not improve tissue oxygenation distal to the stenosis, as compared to the post-stenosis value of 8±0.9 torr with the distal hind limb muscle remaining hypoxic and pale gray in color.

Post-infusion regional tissue oxygen tensions for the stenotic hind limb muscles of Experimental Group A, for 0.5 g/dL and 1.2 g/dL Hb solution infusions, are also provided in FIG. 2. The mean tissue oxygen tensions observed were 20±2.4 torr, associated with an increase in plasma Hb (and total Hb) of 0.5 g/dL, and 29±2.8 torr, associated with an increase in plasma Hb (and total Hb) of 1.2 g/dL. This figure shows that the post-stenotic infusion of hemoglobin solution significantly increased mean tissue oxygen tensions for the hind limb muscle distal to the stenosis, as compared to the post-stenosis mean oxygen tension of 11±1.1 torr, thus alleviating the hypoxic condition.

Improved tissue oxygenation was also demonstrated by a color change of the stenotic muscle from pale gray to a reddish color following hemoglobin solution infusion.

There were no significant differenced between baseline or post-stenotic tissue oxygen tensions when comparing the control group and Experimental Group A. However, there were highly significant increases in tissue oxygen tension in Experimental Group A after the first Hb dose (p<0.01) and after the second Hb dose (p<0.001) when compared to the control group which received equivalent volumes of hetastarch.

A comparison of the mean oxygen tensions are provided in FIG. 2, which shows the relative efficacy of treating hypoxic tissue, distal to a stenosis, with a non-oxygen bearing plasma expander, specifically hetastarch, as compared to treatment with a polymerized hemoglobin blood-substitute. Demonstrated therein, infusion of hetastarch did not improve mean tissue oxygen tension, in muscle tissue distal to a stenosis. In contrast, infusion of a polymerized hemoglobin solution significantly improved mean muscle tissue oxygen tension, in muscle tissue distal to a stenosis, to a normal value when compared to baseline.

EXAMPLE 3
Study of Hemoglobin Solution Flow in Microvasculature Having a RBC Flow Blockade Following induction of anesthesia, the abdomen of a Sprague-Dawley rat was surgically opened to expose the small intestines and associated mesentery. Microcirculation within the mesentery was then observed under a videomicroscope. Identified within the mesentery was a capillary with a thrombosis, with an associated complete obstruction of RBC flow. Measurement of RBC flow through this capillary gave a doppler value of zero, using an optical doppler velocimeter (Texas A&M Microvascular Research Inst.), showing no RBC movement through this capillary.

Polymerized hemoglobin solution (HBOC-201, Biopure Corporation, Boston, Mass.) was labeled with a fluorescent dye, specifically fluorescein isothiocyanate and then intravenously injected into the rat at a location distant from the abdominal cavity.

The hemoglobin in the polymerized hemoglobin solution was labeled with fluorescein isothicyanate (hereinafter "FITC") by employing a modification of the method described by Wilderspin in *Anal. biochem.*, 132: 449 (1982) and Ohshiata in *Anal. biochem.*, 215: 17–23 (1993). A stock solution of FITC label was prepared by dissolving 6.6 g of FITC in 615 mL of 100 mM borate buffer (pH 9.5). Polymerized hemoglobin solution (923 mL at 13 g Hb/dL) was loaded into a nitrogen flushed vessel equilibrated with 512 mL of borate buffer. The FITC/borate buffer was then added at 11.8 mL/min through a static mixer loop to the hemoglobin/borate mixture. The reaction proceeded for 2 hours at room temperature in a nitrogen environment with continuous stirring. Residual FITC was removed by diafiltration with a 30 kD, membrane (Millipore Pellicon, 5 sq. ft.) for seven volume exchanges with a lactate storage solution (pH 7.7). After the last exchange, the system was concentrated to 8.6 g/dL hemoglobin and the material was aliquoted into nitrogen evacuated 10 mL Vacutainer tubes with 60 mL syringes using anaerobic techniques. The tubes were wrapped in tin foil and stored at 4° C. until use. A 10:1 molar ratio of FITC:Hb, used in the reaction, gave a 5:1 ratio of FITC:Hb in the labeled Hb product.

Following injection of the labeled hemoglobin, within about one minute, labelled hemoglobin was then observed entering and flowing through the thrombotic capillary, past the stagnant and stacked aggregation of red blood cells.

The results of this study demonstrate that hemoglobin can flow through microvasculature, through which RBC flow is restricted or precluded, thereby allowing increased oxygen transport by the hemoglobin to tissue associated with the thrombotic capillary wherein there is no RBC flow.

EXAMPLE 4
Synthesis of Stable Polymerized Hemoglobin Blood-Substitute

In this synthesis, portions of the components for the process for a preparing stable polymerized hemoglobin blood-substitute are sufficiently sanitized to produce a sterile product. Sterile is as defined in the art, specifically, that the solution meets United States Pharmacopeia requirements for sterility provided in USP XXII, Section 71, pages 1483–1488.

Further, portions of components that are exposed to the process stream, are usually fabricated or clad with a material that will not react with or contaminate the process stream. Such materials can include stainless steel and other steel alloys, such as Inconel.

A blood-substitute, as defined herein, is a hemoglobin-based oxygen carrying composition which is capable of transporting and transferring oxygen to at least vital organs and tissues and can maintain sufficient intravascular oncotic pressure.

As described in U.S. Pat. No. 5,296,465, samples of bovine whole blood were collected, mixed with a sodium citrate anticoagulant to form a blood solution, and then analyzed for endotoxin levels. The term "endotoxin" refers to the cell-bound lipopolysaccharides produced as a part of the outer layer of bacterial cell walls, which under many conditions are toxic. Endotoxin unit (EU) has been defined by the United States Pharmacopeial Convention of 1983, page 3014, as the activity contained in 0.1 nanograms of U.S. reference standard lot EC-5. One vial of EC-5 contains 10,000 EU.

Each blood solution sample was maintained after collection at a temperature of about 2° C. and then strained to remove large aggregates and particles with a 600 mesh screen.

Prior to pooling, the penicillin level in each blood solution sample was assayed with an assay kit purchased from Difco, Detroit, Mich. using the method entitled "Rapid Detection of Penicillin in Milk" to ensure that penicillin levels in the blood solutions were ≦0.008 units/mL.

The blood solutions samples were then pooled and mixed with depyrogenated aqueous sodium citrate solution to form a 0.2% by weight solution of sodium citrate in bovine whole blood (hereafter "0.2% sodium citrate blood solution").

The 0.2% sodium citrate blood solution was then passed, in-series, through 800μ and 50μ polypropylene filters to remove large blood solution debris of a diameter approximately 50 microns ("μ") or more.

The RBCs were then washed to separate extracellular plasma proteins, such as BSA or IgG, from the RBCs. To wash the RBCs contained in the blood solution, the volume of blood solution in the diafiltration tank was initially diluted by the addition of an equal volume of a filtered isotonic solution to diafiltration tank. The isotonic solution was filtered with a Millipore (Cat # CDUF 050 G1) 10,000 Dalton ultrafiltration membrane. The isotonic solution was composed of 6.0 g/l sodium citrate dihydrate and 8.0 g/l sodium chloride in water-for-injection (WFI). The term WFI is described in *Pharmaceutical Engineering*, 11, 15–23 (1991).

The diluted blood solution was then concentrated back to its original volume by diafiltration through a 0.2 μm hollow fiber (Microgon Krosflo II microfiltration cartridge) diafilter. Concurrently, filtered isotonic solution was added continuously, as makeup, at a rate equal to the rate of filtrate loss through the 0.2 μm diafilter. During diafiltration, components of the diluted blood solution which were significantly smaller in diameter than RBCs, or are fluids such as plasma, passed through the walls of the 0.2 μm diafilter with the filtrate. RBCs, platelets and larger bodies of the diluted blood solution, such as white blood cells, were retained with continuously-added isotonic solution to form a dialyzed blood solution.

During RBC washing, the diluted blood solution was maintained at a temperature between approximately 10° to 25° C. with a fluid pressure at the inlet of the diafilter between about 25 and 30 psi.

RBC washing was complete when the volume of filtrate drained from the diafilter equaled about 600% of the volume of blood solution prior to diluting with filtered isotonic solution.

The dialyzed blood solution was then continuously pumped at a rate of approximately 4 lpm to a Sharples Super Centrifuge, Model # AS-16, fitted with a #28 ringdam. The centrifuge was operating while concurrently being fed dialyzed blood solution, to separate the RBCs from the white blood cells and platelets. During operation, the centrifuge rotated at a rate sufficient to separate the RBCs into a heavy RBC phase, while also separating a substantial portion of the white blood cells (WBCs) and platelets into a light WBC phase, specifically about 15,000 rpm. A fraction of the RBC phase and of the WBC phase were separately and continuously discharged from the centrifuge during operation.

Following separation of the RBCs, the RBCs were lysed to form a hemoglobin-containing solution. A substantial portion of the RBCs were mechanically lysed while discharging the RBCs from the centrifuge. The cell membranes of the RBCs ruptured upon impacting the wall of RBC phase discharge line at an angle to the flow of RBC phase out of the centrifuge, thereby releasing hemoglobin (Hb) from the RBCs into the RBC phase.

The lysed RBC phase then flowed through the RBC phase discharge line into a static mixer (Kenics 1½ inch with 6 elements, Chemineer, Inc.). Concurrent with the transfer of the RBC phase to the static mixer, an equal amount of WFI was also injected into the static mixer, wherein the WFI mixed with the RBC phase. The flow rates of the RBC phase and the WFI into static mixer 40 are each at about 0.25 lpm.

Mixing the RBC phase with WFI in the static mixer produced a lysed RBC colloid. The lysed RBC colloid was then transferred from the static mixer into a Sharples Super Centrifuge (Model # AS-16, Sharples Division of Alfa-Laval Separation, Inc.) which was suitable to separate the Hb from nonhemoglobin RBC components. The centrifuge was rotated at a rate sufficient to separate the lysed RBC colloid into a light Hb phase and a heavy phase. The light phase was composed of Hb and also contained non-hemoglobin components with a density approximately equal to or less than the density of Hb.

The Hb phase was continuously discharged from the centrifuge, through a 0.45μ Millipore Pellicon Cassette, Cat # HVLP 000 C5 microfilter, and into a holding tank in preparation for Hb purification. Cell stroma were then returned with the retinate from the microfilter to the holding tank. During microfiltration, the temperature within the holding tank was maintained at 10° C. or less. When the fluid pressure at the microfilter inlet increased from an initial pressure of about 10 psi to about 25 psi, microfiltration was complete. The Hb microfiltrate was then transferred from the microfilter into the microfiltrate tank.

Subsequently, the Hb microfiltrate was pumped through a 100,000 Millipore Cat # CDUF 050 H1 ultrafilter. A substantial portion of the Hb and water, contained in the Hb microfiltrate, permeated the 100 kD ultrafilter to form an Hb ultrafiltrate, while larger cell debris, such as proteins with a molecular weight above about 100 kD, were retained and recirculated back into the microfiltrate tank. Concurrently, WFI was continuously added to the microfiltrate tank as makeup for water lost in the ultrafiltrate. Generally, cell debris include all whole and fragmented cellular components with the exception of Hb, smaller cell proteins, electrolytes, coenzymes and organic metabolic intermediates. Ultrafiltration continued until the concentration of Hb in the microfiltrate tank was less than 8 grams/liter (g/l). While ultrafiltering the Hb, the internal temperature of the microfiltrate tank was maintained at about 10° C.

The Hb ultrafiltrate was transferred into an ultrafiltrate tank, wherein the Hb ultrafiltrate was then recirculated through a 30,000 Millipore Cat # CDUF 050 T1 ultrafilter to remove smaller cell components, such as electrolytes, coenzymes, metabolic intermediates and proteins less than about 30,000 Daltons in molecular weight, and water from the Hb ultrafiltrate, thereby forming a concentrated Hb solution containing about 100 g Hb/l.

The concentrated Hb solution was then directed from the ultrafiltrate tank onto the media contained in parallel chromatographic columns (2 feet long with an 8 inch inner diameter) to separate the Hb by high performance liquid chromatography. The chromatographic columns contained an anion exchange medium suitable to separate Hb from nonhemoglobin proteins. The anion exchange media was formed from silica gel. The silica gel was exposed to γ-glycidoxy propylsilane to form active epoxide groups and then exposed to $C_3H_7(CH_3)NCl$ to form a quaternary ammonium anion exchange medium. This method of treating silica gel is described in the *Journal of Chromatography*, 120:321–333 (1976).

Each column was pre-treated by flushing the chromatographic columns with a first buffer which facilitated Hb binding. Then 4.52 liters of the concentrated Hb solution were injected into each chromatographic column. After injecting the concentrated Hb solution, the chromatographic columns were then washed by successively directing three different buffers through the chromatographic columns to produce an Hb eluate, by producing a pH gradient within the columns. The temperature of each buffer was about 12.4° C. The buffers were prefiltered through 10,000 Dalton ultrafiltration membrane before injection onto the chromatographic columns.

The first buffer, 20 mM tris-hydroxymethyl aminomethane (Tris) (pH about 8.4 to about 9.4), transported the concentrated Hb solution into the media in the chromatographic columns to bind the Hb. The second buffer, a mixture of the first buffer and a third buffer, with the second buffer having a pH of about 8.3, then adjusted the pH within chromatographic columns to eluate contaminating non-hemoglobin components from the chromatographic columns, while retaining the Hb. Equilibration with the second buffer continued for about 30 minutes at a flow rate of approximately 3.56 lpm per column. The eluate from the second buffer was discarded to waste. The third buffer, 50 mM Tris (pH about 6.5 to about 7.5), then eluated the Hb from chromatographic columns.

The Hb eluate was then directed through a sterile $0.22\mu$ Sartobran Cit # 5232507 G1PH filter to a tank wherein the Hb eluate was collected. The first 3-to-4% of the Hb eluate and the last 3-to-4% of the Hb eluate were directed to waste.

The Hb eluate was further used if the eluate contained less than 0.05 Eu/mL of endotoxin and contained less than 3.3 nM/mL phospholipids. To sixty liters of ultrapure eluate, which had a concentration of 100 g Hb/L, was added 9 L of 1.0M NaCl, 20 mM Tris (pH 8.9) buffer, thereby forming an Hb solution with an ionic strength of 160 mOsm, to reduce the oxygen affinity of the Hb in the Hb solution. The Hb solution was then concentrated at 10° C., by recirculating through the ultrafilter, specifically a 10,000 Dalton Millipore Helicon, Cat # CDUF050G1 filter, until the Hb concentration was 110 g/L.

The Hb solution was then deoxygenated, until the $pO_2$ of the Hb solution was reduced to the level where $HbO_2$ content was about 10%, by recirculating the Hb solution at 12 lpm, through a $0.05\mu$ Hoechst-Celanese Corporation Cat # G-240/40) polypropylene microfilter phase transfer membrane, to form a deoxygenated Hb solution (hereinafter "deoxy-Hb"). Concurrently, a 60 lpm flow of nitrogen gas was directed through the counter side of the phase transfer membrane. During deoxygenation, temperature of the Hb solution was maintained between about 19° C. and about 31° C.

Also during deoxygenation, and subsequently throughout the process, the Hb was maintained in a low oxygen environment to minimize oxygen absorption by the Hb and to maintain an oxygenated Hb (oxyhemoglobin or $HbO_2$) content of less than about 10% in the deoxy-Hb.

The deoxy-Hb was then diafiltered through an ultrafilter with 180 L of a storage buffer, containing 0.2 wt % N-acetyl cysteine, 33 mM sodium phosphate buffer (pH 7.8) having a $pO_2$ of less than 50 torr $pO_2$, to form a oxidation-stabilized deoxy-Hb. Prior to mixing with the deoxy-Hb, the storage buffer was depyrogenated with a 10,000 Dalton Millipore Helicon, Cat # CDUF050G1 depyrogenating filter. The storage buffer was continuously added at a rate approximately equivalent to the fluid loss across the ultrafilter. Diafiltration continued until the volume of fluid lost through diafiltration across the ultrafilter was about three times the initial volume of the deoxy-Hb.

Prior to transferring the oxidation-stabilized deoxy-Hb into a polymerization apparatus, oxygen-depleted WFI was added to the polymerization reactor to purge the polymerization apparatus of oxygen to prevent oxygenation of oxidation-stabilized deoxy-Hb. The amount of WFI added to the polymerization apparatus was that amount which would result in a Hb solution with a concentration of about 40 g Hb/L, when the oxidation-stabilized deoxy-Hb was added to the polymerization reactor. The WFI was then recirculated throughout the polymerization apparatus, to deoxygenate the WFI by flow through a $0.05\mu$ polypropylene microfilter phase transfer membrane (Hoechst-Celanese Corporation Cat # 5PCM-108, 80 sq. ft.) against a counterflow of a pressurized nitrogen. The flow rates of WFI and nitrogen gas, through the phase transfer membrane, were about 18 to 20 lpm and 40 to 60 lpm, respectively.

After the $pO_2$ of the WFI in polymerization apparatus was reduced to less than about 2 torr $pO_2$, the polymerization reactor was blanketed with nitrogen by a flow of about 20 lpm of nitrogen into the head space of the polymerization reactor. The oxidation-stabilized deoxy-Hb was then transferred into the polymerization reactor.

The polymerization was conducted in a 12 mM phosphate buffer with a pH of 7.8, having a chloride concentration less than or equal to about 35 mmolar.

The oxidation-stabilized deoxy-Hb and N-acetyl cysteine were subsequently slowly mixed with the cross-linking agent glutaraldehyde, specifically 29.4 grams of glutaraldehyde for each kilogram of Hb over a five hour period, while heating at 42° C. and recirculating the Hb solution through a Kenics 1½ inch static mixer with 6 elements (Chemineer, Inc.), to form a polymerized Hb solution (hereinafter "poly (Hb)").

Recirculating the oxidation-stabilized deoxy-Hb and the glutaraldehyde through the static mixer caused turbulent flow conditions with generally uniform mixing of the glutaraldehyde with the oxidation-stabilized deoxy-Hb, thereby reducing the potential for forming pockets of deoxy-Hb containing high concentrations of glutaraldehyde. Generally uniform mixing of glutaraldehyde and deoxy-Hb reduced the formation of high molecular weight poly(Hb) (having a molecular weight above 500,000 Daltons) and also permitted faster mixing of glutaraldehyde and deoxy-Hb during polymerization.

In addition, significant Hb intramolecular cross-linking resulted during Hb polymerization as an effect of the presence of N-acetyl cysteine upon the polymerization of Hb.

After polymerization, the temperature of the poly(Hb) in the polymerization reactor was reduced to a temperature between about 8° C. to about 15° C.

The poly(Hb) was then concentrated by recirculating the poly(Hb) through the ultrafilter until the concentration of the poly(Hb) was increased to about 85 g/L. A suitable ultrafilter is a 30,000 Dalton filter (e.g., Millipore Helicon, Cat # CDUF050LT).

Subsequently, the poly(Hb) solution was then mixed with 66.75 g sodium borohydride, to the poly(Hb) and then again recirculated through the static mixer. Specifically, for every nine liters of poly(Hb), one liter of 0.25M sodium borohydride solution was added at a rate of 0.1 to 0.12 lpm.

Prior to adding the sodium borohydride to the poly(Hb), the pH of the poly(Hb) was basified by adjusting pH to a pH of about 10 to preserve the sodium borohydride and to prevent hydrogen gas formation, which can denature proteins during reduction. The pH of the poly(Hb) was adjusted by diafiltering the poly(Hb) with approximately 215 L of depyrogenated, deoxygenated 12 mM sodium borate buffer, having a pH of about 10.4 to about 10.6. The poly(Hb) was diafiltered by recirculating the poly(Hb) from the polymerization reactor through the 30 kD ultrafilter. The sodium borate buffer was added to the poly(Hb) at a rate approximately equivalent to the rate of fluid loss across the ultrafilter from diafiltration. Diafiltration continued until the volume of fluid lost across the ultrafilter from diafiltration was about three times the initial volume of the poly(Hb) in the polymerization reactor.

Following pH adjustment, sodium borohydride solution was added to polymerization reactor to reduce imine bonds in the poly(Hb) to ketimine bonds and to form stable poly(Hb). During the sodium borohydride addition, the poly(Hb) in the polymerization reactor was continuously recirculated through the static mixer and the $0.05\mu$ polypropylene microfilter phase transfer membrane to remove dissolved oxygen and hydrogen. Flow through a static mixer also provided turbulent sodium borohydride flow conditions that rapidly and effectively mixed sodium borohydride with the poly(Hb). The flow rates of poly(Hb) and nitrogen gas through the $0.05\mu$ phase transfer membrane were between about 2.0 to 4.0 lpm and about 12 to 18 lpm, respectively. After completion of the sodium borohydride addition, reduction continued in the polymerization reactor while an agitator contained therein rotated at approximately 75 rotations per minute.

Approximately one hour after the sodium borohydride addition, the stable poly(Hb) was recirculated from the polymerization reactor through the 30 kD ultrafilter until the Hb product concentration was 110 g/l. Following concentration, the pH and electrolytes of the stable poly(Hb) were restored to physiologic levels to form a stable polymerized Hb blood-substitute, by diafiltering the stable poly(Hb), through the 30 kD ultrafilter, with a filtered, deoxygenated, low pH buffer containing 27 mM sodium lactate, 12 mM NAC, 115 mM NaCl, 4 mM KCl, and 1.36 mM $CaCl_2$ in WFI, (pH 5.0). Diafiltration continued until the volume of fluid lost through diafiltration across the ultrafilter was about 6 times the pre-diafiltration volume of the concentrated Hb product.

Stable polymerized hemoglobin (Hb), as defined herein, is polymerized hemoglobin which does not substantially increase or decrease in molecular weight distribution and/or in methemoglobin content during storage periods at suitable storage temperatures for periods of over two years or more, and preferentially for periods of over one years or more, when stored in a suitable relatively low oxygen environment having suitable low oxygen in-leakage. Suitable storage temperatures for storage of more than one year were between about 0° C. and about 40° C. Suitably low oxygen inleakage is in-leakage over a period of about one year, or more, which will result in a methemoglobin concentration of less than about 15% by weight.

After the pH and electrolytes were restored to a physiologic levels, the stable polymerized Hb blood-substitute was then diluted to a concentration of 5.0 g/dl by adding the filtered, deoxygenated low pH buffer to polymerization reactor. The diluted blood substitute was then diafiltered by recirculating from the polymerization reactor through the static mixer and a 100 kD purification filter against a filtered deoxygenated buffer containing 27 mM sodium lactate, 12 mM NAC, 115 mM NaCl, 4 mM KCl, and 1.36 mM $CaCl_2$ in WFI, (pH 7.8). Diafiltration continued until the blood-substitute contained less than or equal to about 10% modified tetrameric and unmodified tetrameric species by GPC when run under dissociating conditions. Modified tetrameric Hb is defined as tetrameric Hb which has been intramolecularly cross-linked to preclude significant dissociation of the Hb tetramers into Hb dimers.

The purification filter was run under conditions of low transmembrane pressure with a restricted permeate line. Following removal of substantial amounts of modified tetrameric Hb and unmodified tetrameric Hb, recirculation of the blood-substitute continued through the 30 kD ultrafilter until the concentration of the blood-substitute was about 130 g/L.

The stable blood-substitute was then stored in a suitable container having a low oxygen environment and a low oxygen in-leakage.

EXAMPLE 5
Polymerized Hemoglobin Analysis

The endotoxin concentration in the hemoglobin product is determined by the method "Kinetic/Turbidimetric LAL 5000 Methodology" developed by Associates of Cape Cod, Woods Hole, Mass., J. Levin et al., *J. Lab. Clin. Med.*, 75:903–911 (1970). Various methods were used to test for any traces of stroma for example, a precipitation assay, Western blotting, Immunoblotting, and enzyme-linked immunosorbent assay (ELISA) for a specific cell membrane protein or glycolipid known by those skilled in the art.

Particulate counting was determined by the method "Particulate Matter in Injections: Large Volume Injections for Single Dose Infusions", U.S Pharmacopeia 22:1596, 1990.

To determine glutaraldehyde concentration, a 400 $\mu$l representative sample of the hemoglobin product was derivitized with dinitrophenylhydrazine and then a 100 $\mu$l aliquot of the derivative solution was injected onto a YMC AQ-303 ODS column at 27° C., at a rate of 1 ml/min., along with a gradient. The gradient consisted of two mobile phases, 0.1% trifluoroacetic acid (TFA) in water and 0.08% TFA in acetonitrile. The gradient flow consisted of a constant 60% 0.08% TFA in acetonitrile for 6.0 minutes, a linear gradient to 85% 0.08% TFA in acetonitrile over 12 minutes, a linear gradient to 100% 0.08% TFA in acetonitrile over 4 minutes hold at 100% 0.08% TFA in acetonitrile for 2 minutes and re-equilibrate at 45% 0.1% TFA in water. Ultraviolet detection was measured at @360 nm.

To determine N-acetyl cysteine concentration, an aliquot of hemoglobin product was diluted 1:100 with degassed sodium phosphate in water and 50 $\mu$l was injected onto a YMC AQ-303 ODS column with a gradient. The gradient buffers consisted of a sodium phosphate in water solution and a mixture of 80% acetonitrile in water with 0.05% TFA. The gradient flow consisted of 100% sodium phosphate in water for 15 minutes, then a linear gradient to 100% mixture of 80% acetonitrile and 0.05% TFA over 5 minutes, with a hold for 5 minutes. The system was then re-equilibrated at 100% sodium phosphate for 20 minutes.

Phospholipid analysis was done by a method based on procedures contained in the following two papers: Kolarovic et al., "A Comparison of Extraction Methods for the Isolation of Phospholipids from Biological Sources", *Anal. Biochem.*, 156:244–250, 1986 and Duck-Chong, C. G., "A Rapid Sensitive Method for Determining Phospholipid Phosphorus Involving Digestion With Magnesium Nitrate", *Lipids*, 14:492–497, 1979.

Osmolarity was determined by analysis on an Advanced Cryomatic Osmometer, Model #3C2, Advanced Instruments, Inc., Needham, Mass.

Total hemoglobin, methemoglobin and oxyhemoglobin concentrations were determined on an Co-Oximeter Model #482, from Instrumentation Laboratory, Lexington, Mass.

$Na^+$, $K^+$, $Cl^-$, $Ca^{++}$, $pO_2$ concentration was determined by a Novastat Profile 4, Nova Biomedical Corporation, Waltham, Mass.

Oxygen binding constant, $P_{50}$ was determined by a Hemox-Analyzer, TCS Corporation, Southhampton, Pa.

Temperature and pH were determined by standard methods known by those skilled in the art.

Molecular weight (M.W.) was determined by conducting gel permeation chromatography (GPC) on the hemoglobin products under dissociating conditions. A representative sample of the hemoglobin product was analyzed for molecular weight distribution. The hemoglobin product was diluted to 4 mg/ml within a mobile phase buffer of 50 mM Bis-Tris (pH 6.5), 750 mM $MgCl_2$, and 0.1 mM EDTA. This buffer serves to dissociate Hb tetramer into dimers, that have not been crosslinked to other Hb dimers through intramolecular or intermolecular crosslinks, from the poly-Hb. The diluted sample was injected onto a TosoHaas G3000SW column. Flow rate was 0.5 ml/min. and ultraviolet detection was recorded at 280 nm.

The results of the above tests on human (HEMOPURE™2) Hb blood-substitutes are summarized in Table I.

TABLE I

| PARAMETER | RESULTS |
|---|---|
| pH (18–22° C.) | Physiologically acceptable pH |
| Endotoxin | <0.5 EU/ml |
| Sterility Test | Meets Test |
| Phospholipids[a] | <3.3 nm/mL |
| Total Hemoglobin | 12.0–14.0 g/dL |
| Methemoglobin | <15% |
| Oxyhemoglobin | ≦10% |
| Sodium, $Na^+$ | 145–160 mM |
| Potassium, $K^+$ | 3.5–5.5 mM |
| Chloride, $Cl^-$ | 105–120 mM |
| Calcium, $Ca^{++}$ | 0.5–1.5 mM |
| Boron | ≦10 ppm |
| Osmolality | 290–310 mOsm |
| Glutaraldehyde | <3.5 μg/ml |
| N-acetyl-L-cysteine | ≦0.02% |
| M.W. > 500,000 | ≦15% |
| M.W. ≦ 65,000 | ≦10% |
| M.W. ≦ 32,000 | ≦5% |
| Particulate Content ≧ 10μ | <50/mL |
| Particulate Content ≧ 25μ | <5/mL |

[a]-measured in Hb before polymerization

Equivalents

Those skilled in the art will recognize, or be able to ascertain using no more than routine experimentation, many equivalents to specific embodiments of the invention described specifically herein. Such equivalents are intended to be encompassed in the scope of the following claims.

The invention claimed is:

1. A stable polymerized hemoglobin human blood-substitute, comprising mammalian hemoglobin, with a concentration between 120 to 140 grams per liter of solution, wherein:

a) methemoglobin content is less than 15% by weight;

b) oxyhemoglobin content is less than or equal to 10 percent by weight;

c) endotoxin concentration is less than 0.5 Endotoxin units per milliliter;

d) 15% by weight, or less, of the polymerized hemoglobin has a molecular weight of over 500,000 Daltons; and e) 10% by weight, or less, of the polymerized hemoglobin has a molecular weight equal to or less than 65,000 Daltons.

* * * * *